(12) United States Patent
Fletcher et al.

(10) Patent No.: US 9,549,700 B2
(45) Date of Patent: Jan. 24, 2017

(54) BIOLOGICAL FLUID SAMPLING TRANSFER DEVICE AND BIOLOGICAL FLUID SEPARATION AND TESTING SYSTEM

(71) Applicant: Becton, Dickinson and Company, Franklin Lakes, NJ (US)

(72) Inventors: Gary D. Fletcher, Sparta, NJ (US); Craig A. Gelfand, Jackson, NJ (US); Daniel J. Marchiarullo, Morris Plains, NJ (US); C. Mark Newby, Tuxedo, NY (US); Ashley Rachel Rothenberg, Morris Plains, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 257 days.

(21) Appl. No.: 14/251,693

(22) Filed: Apr. 14, 2014

(65) Prior Publication Data
US 2014/0309557 A1    Oct. 16, 2014

Related U.S. Application Data

(60) Provisional application No. 61/811,918, filed on Apr. 15, 2013.

(51) Int. Cl.
*A61B 5/00* (2006.01)
*A61B 5/15* (2006.01)
(Continued)

(52) U.S. Cl.
CPC ....... *A61B 5/150213* (2013.01); *A61B 5/1411* (2013.01); *A61B 5/151* (2013.01);
(Continued)

(58) Field of Classification Search
CPC ... A61B 5/1411; A61B 5/14514; A61B 5/151; A61B 5/15115; A61B 5/15117; A61B 5/15142; A61B 5/151144; A61B 5/150213; A61B 5/150305; A61B 5/150343; A61B 5/150755
See application file for complete search history.

(56) References Cited

U.S. PATENT DOCUMENTS

| 3,322,114 A | 5/1967 | Portnoy et al. |
| 3,640,393 A | 2/1972 | Hurtig |
| (Continued) | | |

FOREIGN PATENT DOCUMENTS

| CN | 1382966 A | 12/2002 |
| CN | 101102847 A | 1/2008 |
| (Continued) | | |

OTHER PUBLICATIONS

Membrane Separation Technology for Research and Quality Control, Sartorius AG, Separation Technology, Laboratory Filtration; Mar. 1, 1997.

*Primary Examiner* — Max Hindenburg
(74) *Attorney, Agent, or Firm* — The Webb Law Firm

(57) ABSTRACT

A blood separation and testing system for a blood sample is disclosed. The blood separation and testing system includes a blood sampling transfer device adapted to receive a blood sample, a blood separation device, and a blood testing device. The blood separation device is adapted to receive a portion of the blood sampling transfer device such that with the blood sampling transfer device received within the blood separation device and a rotational force applied to the blood sampling transfer device, a plasma portion of the blood sample is separated from a cellular portion of the blood sample. The blood testing device is adapted to receive a portion of the blood sampling transfer device to analyze the plasma portion of the blood sample and obtain test results.

13 Claims, 11 Drawing Sheets

(51) Int. Cl.

| | | |
|---|---|---|
| *G01N 33/49* | (2006.01) | |
| *A61M 1/34* | (2006.01) | |
| *G01N 1/28* | (2006.01) | |
| *G01N 1/40* | (2006.01) | |
| *G01N 1/34* | (2006.01) | |
| *B01L 3/00* | (2006.01) | |
| *B04B 7/08* | (2006.01) | |
| *A61B 5/151* | (2006.01) | |
| *A61B 5/157* | (2006.01) | |

(52) U.S. Cl.
CPC ........ *A61B 5/157* (2013.01); *A61B 5/150022* (2013.01); *A61B 5/15101* (2013.01); *A61B 5/15105* (2013.01); *A61B 5/15144* (2013.01); *A61B 5/15198* (2013.01); *A61B 5/150221* (2013.01); *A61B 5/150267* (2013.01); *A61B 5/150305* (2013.01); *A61B 5/150343* (2013.01); *A61B 5/150351* (2013.01); *A61B 5/150412* (2013.01); *A61B 5/150748* (2013.01); *A61B 5/150755* (2013.01); *A61B 5/150778* (2013.01); *A61M 1/34* (2013.01); *B01L 3/502* (2013.01); *B01L 3/5021* (2013.01); *B04B 7/08* (2013.01); *G01N 1/28* (2013.01); *G01N 1/34* (2013.01); *G01N 1/4005* (2013.01); *G01N 1/4077* (2013.01); *G01N 33/491* (2013.01); *A61B 5/150435* (2013.01); *A61B 5/150442* (2013.01); *A61B 5/150969* (2013.01); *B01L 2200/0631* (2013.01); *B01L 2200/10* (2013.01); *B01L 2300/0681* (2013.01); *B01L 2400/0478* (2013.01); *G01N 2001/4016* (2013.01); *G01N 2001/4088* (2013.01)

(56) References Cited

U.S. PATENT DOCUMENTS

| | | | |
|---|---|---|---|
| 4,511,349 A | 4/1985 | Nielsen et al. | |
| 4,627,445 A | 12/1986 | Garcia et al. | |
| 5,055,203 A | 10/1991 | Columbus | |
| 5,163,442 A | 11/1992 | Ono | |
| 5,219,999 A | 6/1993 | Suzuki et al. | |
| 5,422,018 A | 6/1995 | Saunders et al. | |
| 5,636,640 A | 6/1997 | Staehlin | |
| 5,726,026 A | 3/1998 | Wilding et al. | |
| 5,839,715 A | 11/1998 | Leinsing | |
| 5,922,591 A | 7/1999 | Anderson et al. | |
| 6,074,183 A | 6/2000 | Allen et al. | |
| 6,264,619 B1 | 7/2001 | Ferguson | |
| 6,506,167 B1 | 1/2003 | Ishimito et al. | |
| 6,537,242 B1* | 3/2003 | Palmer | A61M 37/0015 600/309 |
| 6,613,064 B2* | 9/2003 | Rutynowski | A61B 5/1411 606/182 |
| 6,869,405 B2 | 3/2005 | Marsden | |
| 7,001,344 B2* | 2/2006 | Freeman | A61B 5/1411 600/583 |
| 7,014,625 B2* | 3/2006 | Bengtsson | A61M 5/14248 604/131 |
| 8,158,410 B2 | 4/2012 | Tang et al. | |
| 8,211,036 B2* | 7/2012 | Schraga | A61B 5/1411 600/573 |
| 8,469,984 B2* | 6/2013 | Ruan | A61B 5/1411 606/181 |
| 8,764,657 B2* | 7/2014 | Curry | A61B 17/34 600/309 |
| 9,295,417 B2* | 3/2016 | Haghgooie | A61B 5/1411 |
| 2002/0009015 A1 | 1/2002 | Laugharn, Jr. et al. | |
| 2002/0143298 A1 | 10/2002 | Marsden | |
| 2003/0134416 A1 | 7/2003 | Yamanishi et al. | |
| 2004/0142463 A1 | 7/2004 | Walker et al. | |
| 2004/0143226 A1 | 7/2004 | Marsden | |
| 2004/0230216 A1 | 11/2004 | Levaughn et al. | |
| 2005/0069459 A1 | 3/2005 | Ahn et al. | |
| 2005/0214927 A1 | 9/2005 | Haley | |
| 2006/0029923 A1 | 2/2006 | Togawa et al. | |
| 2006/0240964 A1 | 10/2006 | Lolachi et al. | |
| 2007/0031283 A1 | 2/2007 | Davis et al. | |
| 2007/0160503 A1 | 7/2007 | Sethu et al. | |
| 2008/0135502 A1 | 6/2008 | Pyo et al. | |
| 2008/0240990 A1 | 10/2008 | Flaherty | |
| 2009/0004060 A1 | 1/2009 | Omuro et al. | |
| 2009/0136982 A1 | 5/2009 | Tang et al. | |
| 2009/0181411 A1 | 7/2009 | Battrell et al. | |
| 2009/0204026 A1 | 8/2009 | Crawford et al. | |
| 2010/0089815 A1 | 4/2010 | Zhang et al. | |
| 2010/0093551 A1 | 4/2010 | Montagu | |
| 2010/0198108 A1 | 8/2010 | Alden | |
| 2010/0241031 A1 | 9/2010 | Lai | |
| 2011/0124130 A1 | 5/2011 | Wagner et al. | |
| 2011/0124984 A1 | 5/2011 | Rostaing | |
| 2012/0152858 A1 | 6/2012 | Yang | |
| 2012/0275955 A1 | 11/2012 | Haghgooie et al. | |
| 2012/0277696 A1 | 11/2012 | Gonzalez-Zugasti et al. | |
| 2012/0277697 A1 | 11/2012 | Haghgooie et al. | |
| 2013/0026085 A1 | 1/2013 | Samsoondar | |
| 2013/0052675 A1 | 2/2013 | Karlsson et al. | |
| 2013/0082012 A1 | 4/2013 | Lean et al. | |
| 2013/0086980 A1 | 4/2013 | Gadini et al. | |
| 2013/0175213 A1 | 7/2013 | Dorrer et al. | |
| 2013/0209331 A1 | 8/2013 | Rodenfels et al. | |

FOREIGN PATENT DOCUMENTS

| | | |
|---|---|---|
| CN | 101332320 A | 12/2008 |
| CN | 102764133 A | 11/2012 |
| DE | 202008010918 U1 | 1/2009 |
| EP | 0376168 A2 | 7/1990 |
| EP | 0747105 A2 | 12/1996 |
| EP | 1096254 A2 | 5/2001 |
| EP | 1106065 A2 | 6/2001 |
| EP | 1477804 A1 | 11/2004 |
| EP | 1602329 A1 | 12/2005 |
| EP | 1627651 A2 | 2/2006 |
| EP | 2264453 A1 | 12/2010 |
| EP | 2413138 A2 | 2/2012 |
| FR | 2929135 A1 | 10/2009 |
| FR | 2977808 A1 | 1/2013 |
| JP | 2004361419 A | 12/2004 |
| WO | 9309710 A1 | 5/1993 |
| WO | 2005018710 A2 | 3/2005 |
| WO | 2006047831 A1 | 5/2006 |
| WO | 2007002579 A2 | 1/2007 |
| WO | 2009123592 A1 | 10/2009 |
| WO | 2011040874 A1 | 4/2011 |
| WO | 2012121686 A1 | 9/2012 |

* cited by examiner

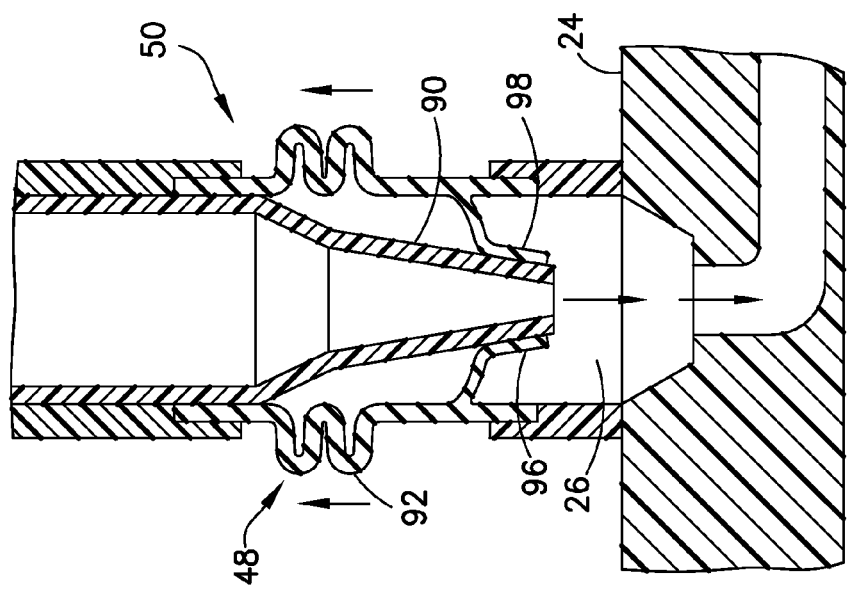
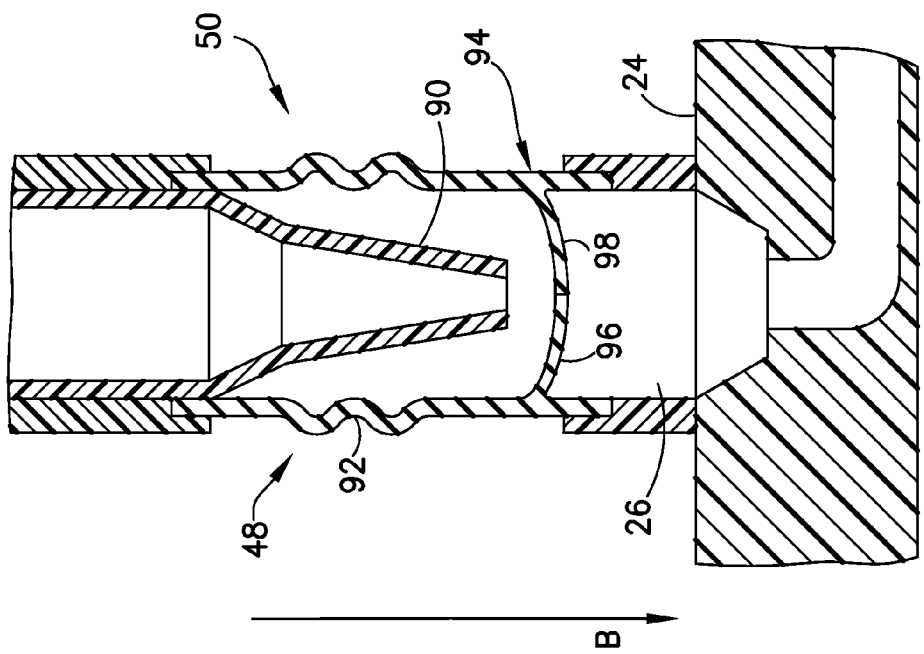

BIOLOGICAL FLUID SAMPLING TRANSFER DEVICE AND BIOLOGICAL FLUID SEPARATION AND TESTING SYSTEM

CROSS REFERENCE TO RELATED APPLICATIONS

The present application claims priority to U.S. Provisional Application No. 61/811,918, filed Apr. 15, 2013, entitled "Medical Device for Collection of a Biological Sample", the entire disclosure of which is hereby incorporated by reference in its entirety.

BACKGROUND OF THE INVENTION

1. Field of the Disclosure

The present disclosure relates generally to devices, assemblies, and systems adapted for use with capillary access devices. More particularly, the present disclosure relates to devices, assemblies, and systems adapted for collecting biological samples for use in point-of-care testing.

2. Description of the Related Art

Blood sampling is a common health care procedure involving the withdrawal of at least a drop of blood from a patient. Blood samples are commonly taken from hospitalized, homecare, and emergency room patients either by finger stick, heel stick, or venipuncture. Blood samples may also be taken from patients by venous or arterial lines. Once collected, blood samples may be analyzed to obtain medically useful information including chemical composition, hematology, or coagulation, for example.

Blood tests determine the physiological and biochemical states of the patient, such as disease, mineral content, drug effectiveness, and organ function. Blood tests may be performed in a clinical laboratory or at the point-of-care near the patient. One example of point-of-care blood testing is the routine testing of a patient's blood glucose levels which involves the extraction of blood via a finger stick and the mechanical collection of blood into a diagnostic cartridge. Thereafter, the diagnostic cartridge analyzes the blood sample and provides the clinician a reading of the patient's blood glucose level. Other devices are available which analyze blood gas electrolyte levels, lithium levels, and ionized calcium levels. Some other point-of-care devices identify markers for acute coronary syndrome (ACS) and deep vein thrombosis/pulmonary embolism (DVT/PE).

Despite the rapid advancement in point-of-care testing and diagnostics, blood sampling techniques have remained relatively unchanged. Blood samples are frequently drawn using hypodermic needles or vacuum tubes attached to a proximal end of a needle or a catheter assembly. In some instances, clinicians collect blood from a catheter assembly using a needle and syringe that is inserted into the catheter to withdraw blood from a patient through the inserted catheter. These procedures utilize needles and vacuum tubes as intermediate devices from which the collected blood sample is typically withdrawn prior to testing. These processes are thus device intensive, utilizing multiple devices in the process of obtaining, preparing, and testing blood samples. Each additional device increases the time and cost of the testing process.

Point-of-care testing devices allow for a blood sample to be tested without needing to send the blood sample to a lab for analysis. Thus, it is desirable to create a device that provides an easy, safe, reproducible, and accurate process with a point-of-care testing system.

SUMMARY OF THE INVENTION

The present disclosure provides a biological fluid separation and testing system, such as a blood separation and testing system, for a blood sample. The biological fluid separation and testing system includes a biological fluid sampling transfer device, such as a blood sampling transfer device, adapted to receive a blood sample, a blood separation device, and a blood testing device. The blood separation device is adapted to receive a portion of the blood sampling transfer device such that with the blood sampling transfer device received within the blood separation device and a rotational force applied to the blood sampling transfer device, a plasma portion of the blood sample is separated from a cellular portion of the blood sample. The blood testing device is adapted to receive a portion of the blood sampling transfer device to analyze the plasma portion of the blood sample and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, and it is capable of transferring pure plasma to a point-of-care testing device. The clinician may collect and separate the blood sample and then immediately transfer the plasma portion to the point-of-care testing device without further manipulation. This enables collection and transfer of plasma to the point-of-care testing device without exposure to blood. Further, for tests which only require small amounts of blood, it eliminates the waste associated with blood collection and plasma separation with an evacuated tube. Also, the blood sampling transfer device of the present disclosure incorporates the concepts of lancing, blood collection, and blood separation.

In accordance with an embodiment of the present invention, a biological fluid sampling transfer device includes a housing having a resiliently deformable upper portion, a lower portion removably connectable to the upper portion, the lower portion having an inlet port, an outlet port, and a flow channel, with the inlet port and the outlet port in fluid communication via the flow channel. The upper portion is transitionable between an undeformed position and a deformed position. The device also includes a puncturing element, a portion of which is disposed within the housing and adapted for movement between a pre-actuated position wherein the puncturing element is retained within the housing and a puncturing position wherein the puncturing element extends through the inlet port of the lower portion of the housing.

In certain configurations, the blood sampling transfer device is adapted to receive a multi-component blood sample. The multi-component blood sample may include a first cellular component and a second plasma component. The flow channel may be adapted to receive the blood sample via the inlet port.

In other configurations, actuation of the upper portion from the undeformed position to the deformed position moves the puncturing element from a pre-actuated position to a puncturing position. After the puncturing element moves to the puncturing position, the upper portion returns to its undeformed position and returns the puncturing element to the pre-actuated position. With the blood sample received within the flow channel, the lower portion is removable from the upper portion. In certain configurations, the device also includes an adhesive disposed on an outside surface of the lower portion. The device may also include a check valve in the upper portion.

In accordance with another embodiment of the present invention, a biological fluid sampling transfer device adapted to receive a multi-component blood sample includes a housing having a resiliently deformable upper portion and a lower portion removably connectable to the upper portion. The lower portion includes an inlet port, an outlet port, and a flow channel, with the inlet port and the outlet port in fluid communication via the flow channel. The flow channel is adapted to receive the blood sample via the inlet port, and the upper portion is transitionable between an undeformed position and a deformed position. The device also includes a puncturing element, a portion of which is disposed within the housing and adapted for movement between a pre-actuated position wherein the puncturing element is retained within the housing and a puncturing position wherein the puncturing element extends through the inlet port of the lower portion of the housing. Actuation of the upper portion from the undeformed position to the deformed position moves the lancet from the pre-actuated position to the puncturing position. After the puncturing element moves to the puncturing position, the upper portion returns to the undeformed position and the lancet returns to the pre-actuated position.

In certain configurations, with the blood sample received within the flow channel, the lower portion is removable from the upper portion. Optionally, the device may also include an adhesive disposed on an outside surface of the lower portion. The device may also include a check valve in the upper portion.

In accordance with yet another embodiment of the present invention, a biological fluid separation and testing system for a multi-component blood sample includes a blood sampling transfer device adapted to receive the blood sample. The blood sampling transfer device includes a housing having a resiliently deformable upper portion, and a lower portion removably connectable to the upper portion. The lower portion includes an inlet port, an outlet port, and a flow channel, with the inlet port and the outlet port in fluid communication via the flow channel. The flow channel is adapted to receive the blood sample via the inlet port, and the upper portion is transitionable between an undeformed position and a deformed position. The device also includes a puncturing element, a portion of which is disposed within the housing and adapted for movement between a pre-actuated position wherein the puncturing element is retained within the housing and a puncturing position wherein the puncturing element extends through the inlet port of the lower portion of the housing. Actuation of the upper portion from the undeformed position to the deformed position moves the lancet from the pre-actuated position to the puncturing position. After the puncturing element moves to the puncturing position, the upper portion returns to the undeformed position and the puncturing element returns to the pre-actuated position. The system also includes a blood testing device having a receiving port adapted to receive the outlet port of the lower portion of the housing of the blood sampling transfer device for closed transfer of a portion of the blood sample from the blood sampling transfer device to the blood testing device via the outlet port.

In certain configurations, the blood testing device may be a point-of-care testing device. When the blood sampling transfer device is received within the receiving port of the blood testing device, actuation of the upper portion from the undeformed position to the deformed position transfers the blood sample from the blood sampling transfer device to the blood testing device via the outlet port. When the blood sample is received within the flow channel, the lower portion is removable from the upper portion.

In other configurations, the system also includes a blood separation device, and when the lower portion is removed from the upper portion, the lower portion is receivable within the blood separation device. When the lower portion is received within the blood separation device, the blood sample contained within the lower portion is separated. Optionally, a portion of the housing includes a sample stabilizer.

BRIEF DESCRIPTION OF THE DRAWINGS

The above-mentioned and other features and advantages of this disclosure, and the manner of attaining them, will become more apparent and the disclosure itself will be better understood by reference to the following descriptions of embodiments of the disclosure taken in conjunction with the accompanying drawings, wherein:

FIG. 11 is a cross-sectional view of a valve of a biological fluid sampling transfer device in accordance with an embodiment of the present invention, with the valve in a closed position.

FIG. 12 is a cross-sectional view of a valve of a biological fluid sampling transfer device in accordance with an embodiment of the present invention, with the valve in an open position.

Corresponding reference characters indicate corresponding parts throughout the several views. The exemplifications set out herein illustrate exemplary embodiments of the disclosure, and such exemplifications are not to be construed as limiting the scope of the disclosure in any manner.

DETAILED DESCRIPTION

Figure 1:
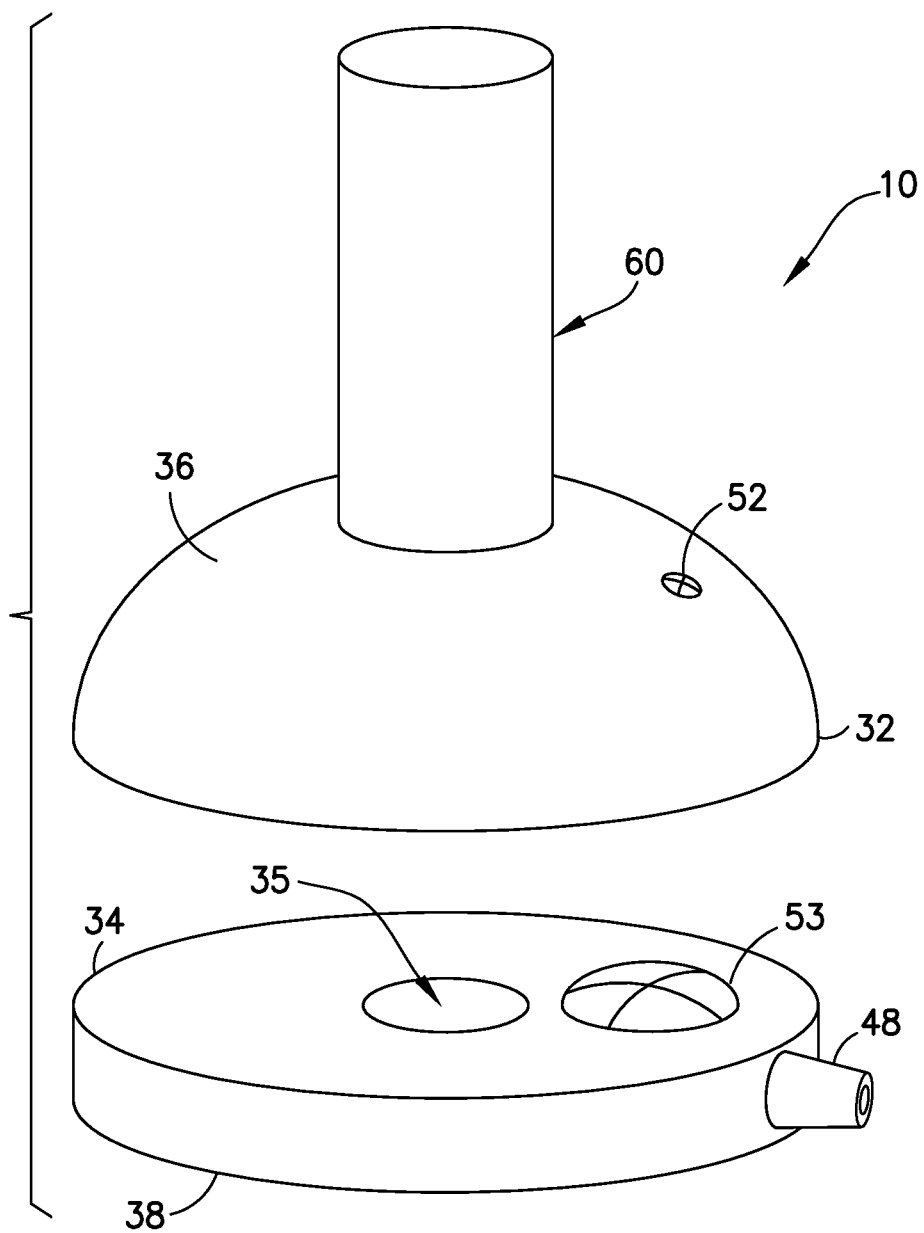
FIG. 1 is an exploded, perspective view of a biological fluid sampling transfer device in accordance with an embodiment of the present invention.
Figure 2:
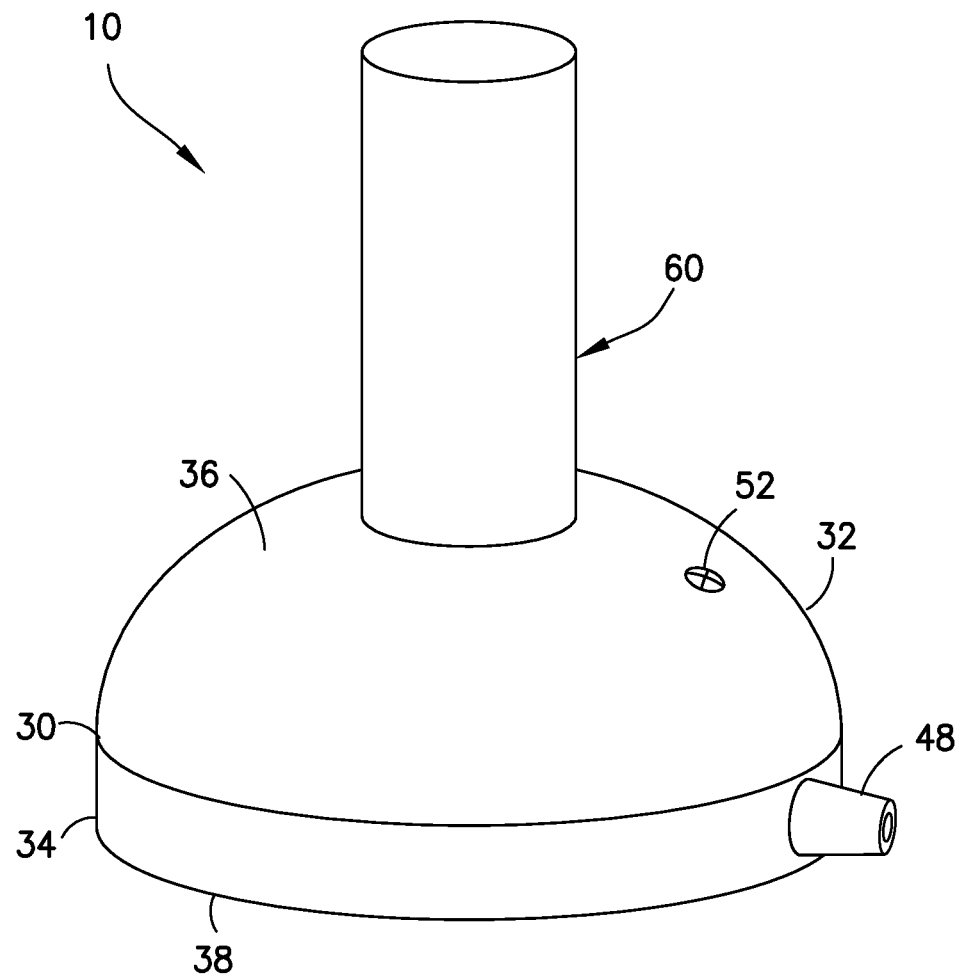
FIG. 2 is an assembled, perspective view of a biological fluid sampling transfer device in accordance with an embodiment of the present invention.

The following description is provided to enable those skilled in the art to make and use the described embodiments contemplated for carrying out the invention. Various modifications, equivalents, variations, and alternatives, however, will remain readily apparent to those skilled in the art. Any and all such modifications, variations, equivalents, and alternatives are intended to fall within the spirit and scope of the present invention.

For purposes of the description hereinafter, the terms "upper", "lower", "right", "left", "vertical", "horizontal", "top", "bottom", "lateral", "longitudinal", and derivatives thereof shall relate to the invention as it is oriented in the drawing figures. However, it is to be understood that the invention may assume alternative variations and step sequences, except where expressly specified to the contrary. It is also to be understood that the specific devices and processes illustrated in the attached drawings, and described in the following specification, are simply exemplary embodiments of the invention. Hence, specific dimensions and other physical characteristics related to the embodiments disclosed herein are not to be considered as limiting.

Various point-of-care testing devices are known in the art. Such point-of-care testing devices include test strips, glass slides, diagnostic cartridges, or other testing devices for testing and analysis. Test strips, glass slides, and diagnostic cartridges are point-of-care testing devices that receive a blood sample and test that blood for one or more physiological and biochemical states. There are many point-of-care devices that use cartridge based architecture to analyze very small amounts of blood bedside without the need to send the sample to a lab for analysis. This saves time in getting results over the long run but creates a different set of challenges versus the highly routine lab environment. Examples of such testing cartridges include the i-STAT® testing cartridge from the Abbot group of companies. Testing cartridges such as the i-STAT® cartridges may be used to test for a variety of conditions including the presence of chemicals and electrolytes, hematology, blood gas concentrations, coagulation, or cardiac markers. The results of tests using such cartridges are quickly provided to the clinician.

However, the samples provided to such point-of-care testing cartridges are currently manually collected with an open system and transferred to the point-of-care testing cartridge in a manual manner that often leads to inconsistent results, or failure of the cartridge leading to a repeat of the sample collection and testing process, thereby negating the advantage of the point-of-care testing device. Accordingly, a need exists for a system for collecting and transferring a sample to a point-of-care testing device that provides safer, reproducible, and more accurate results. Accordingly, a point-of-care collecting and transferring system of the present disclosure will be described hereinafter. A system of the present disclosure enhances the reliability of the point-of-care testing device by: 1) incorporating a more closed type of sampling and transfer system; 2) minimizing open exposure of the sample; 3) improving sample quality; 4) improving the overall ease of use; and 5) separating the sample at the point of collection.

FIGS. 1-7 illustrate an exemplary embodiment of the present disclosure. The biological fluid sampling transfer device of the present disclosure incorporates the concepts of lancing, blood collection, and blood separation. Referring to FIGS. 1-7, a biological fluid sampling transfer device 10, such as a blood sampling transfer device, of the present disclosure is adapted to receive a blood sample 12 (FIGS. 6, 7, and 9) having a cellular portion 14 and a plasma portion 16.

Figure 8:
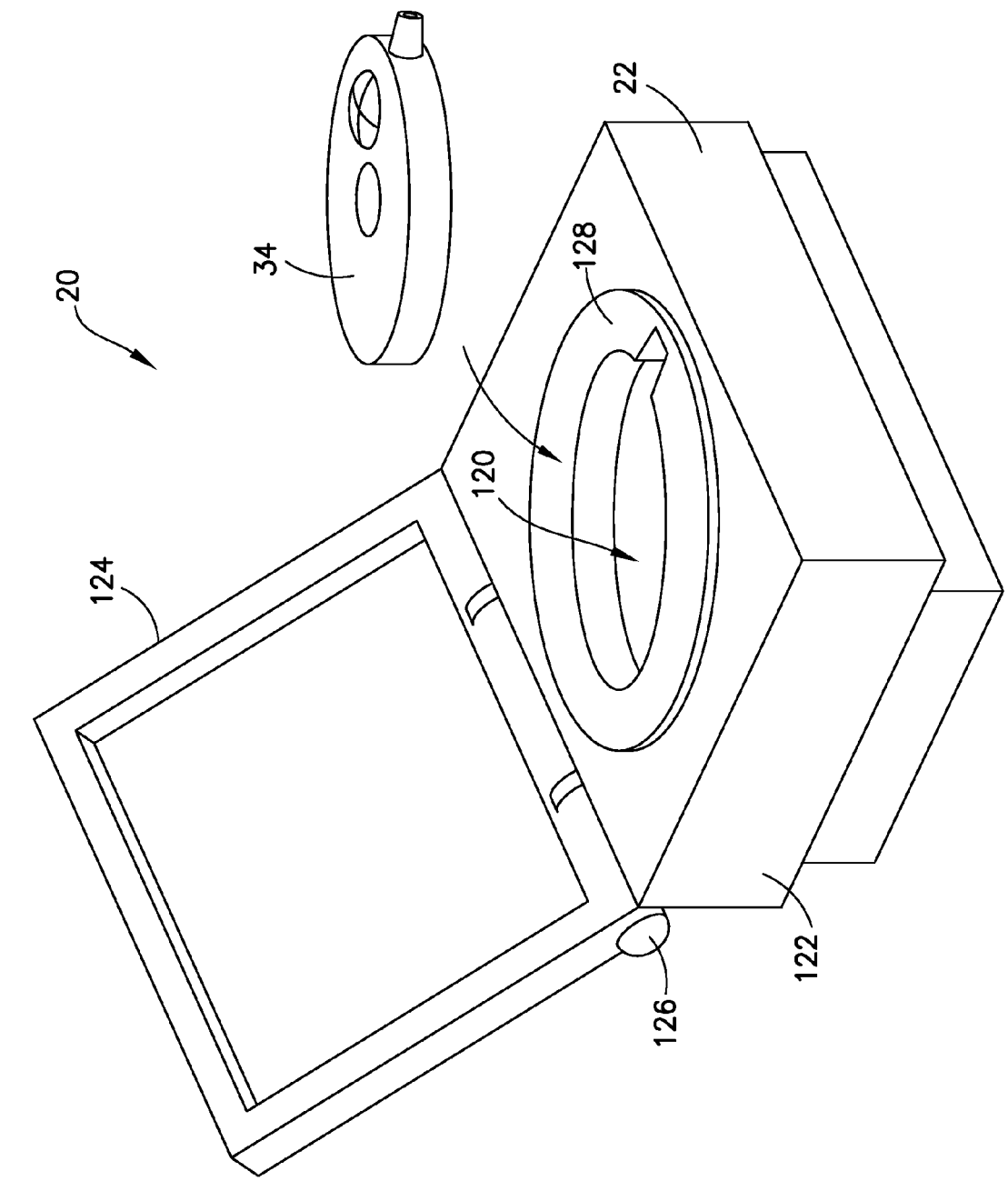
FIG. 8 is a perspective view of a biological fluid separation system in accordance with an embodiment of the present invention.
Figure 9:
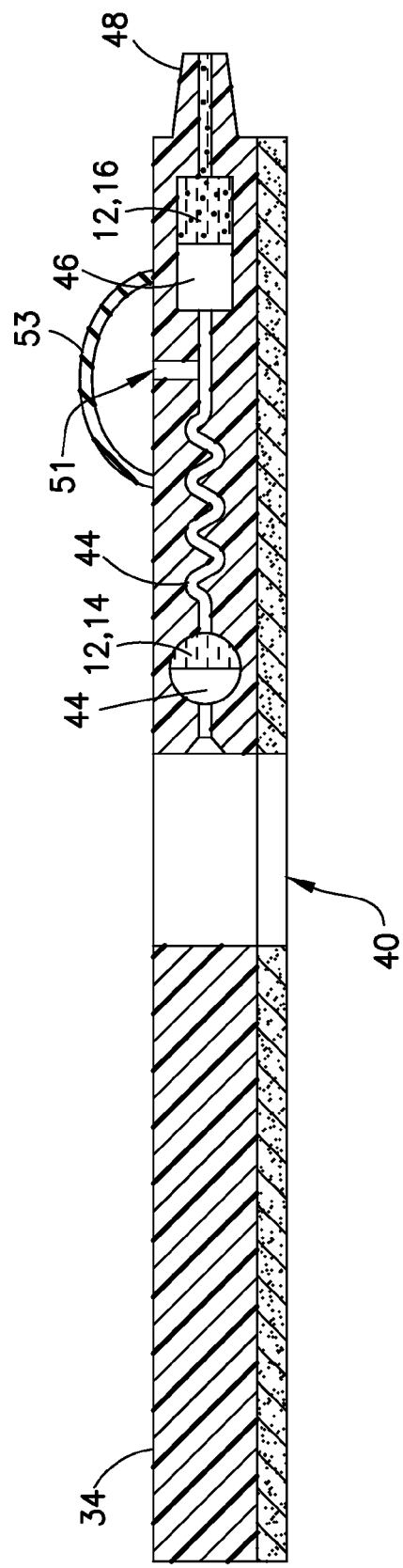
FIG. 9 is a cross-sectional view of a lower portion of the biological fluid sampling transfer device of FIG. 8 in accordance with an embodiment of the present invention.
Figure 10:
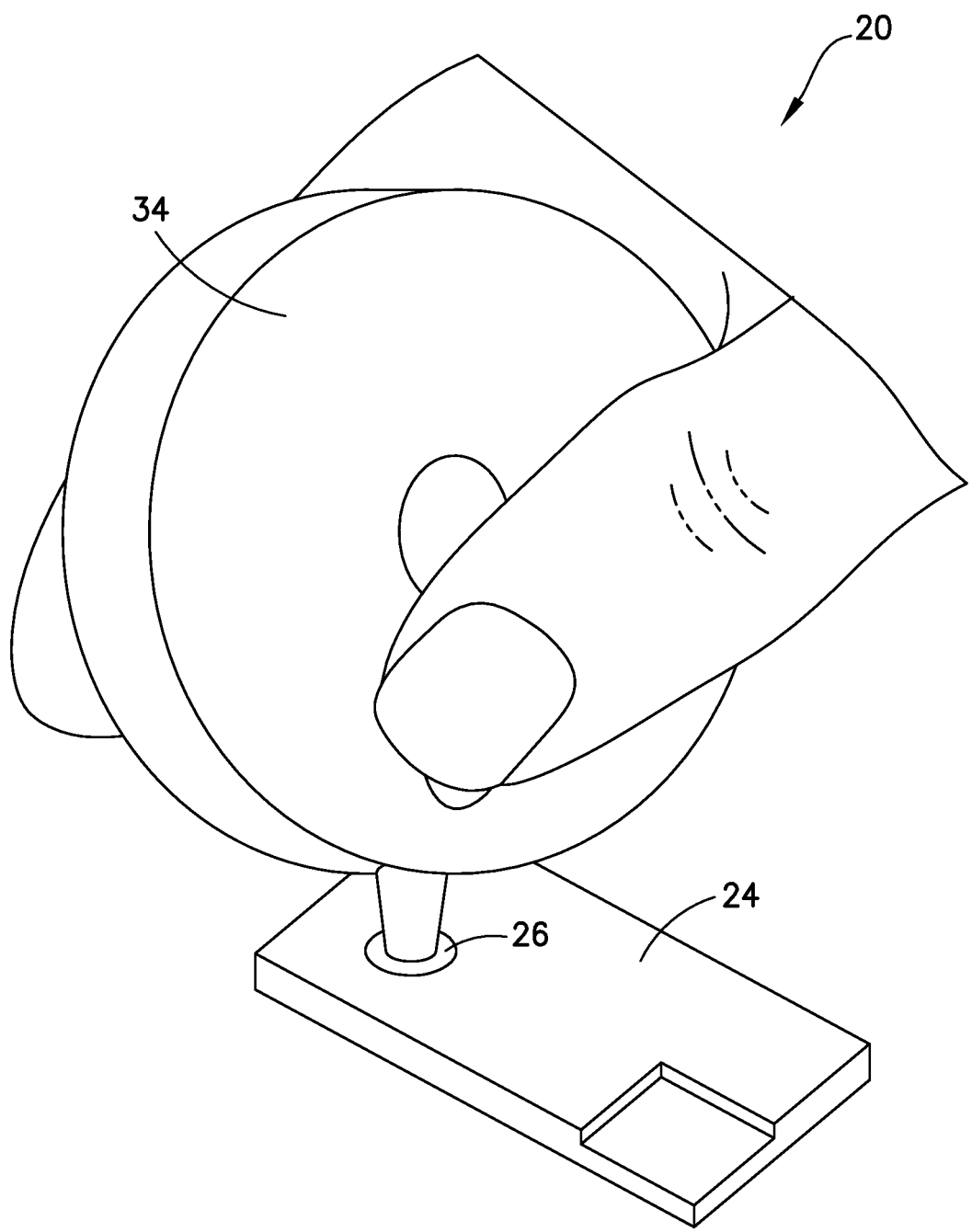
FIG. 10 is a perspective view of a lower portion of the biological fluid sampling transfer device and a point-of-care testing device in accordance with an embodiment of the present invention.

FIGS. 8-10 illustrate an exemplary embodiment of the present disclosure. Referring to FIGS. 8-10, a biological fluid separation and testing system 20, such as a blood separation and testing system, of the present disclosure for a blood sample 12 includes a blood sampling transfer device 10 adapted to receive a blood sample 12, a blood separation device or centrifuge 22, and a blood testing device or point-of-care testing device 24. The centrifuge 22 is adapted to receive a portion of the blood sampling transfer device 10 such that with the blood sampling transfer device 10 received within the centrifuge 22 and a rotational force applied to the blood sampling transfer device 10, a plasma portion 16 of the blood sample 12 is separated from a cellular portion 14 of the blood sample 12. The blood testing device 24 is adapted to receive a portion of the blood sampling transfer device 10 to analyze the plasma portion 16 of the blood sample 12 and obtain test results.

Some of the advantages of the blood sampling transfer device and the blood separation and testing system of the present disclosure over prior systems are that it is a closed system which reduces blood sample exposure, it provides passive and fast mixing of the blood sample with a sample stabilizer, and it is capable of transferring pure plasma to the point-of-care testing device 24. The clinician may collect and separate the blood sample and then immediately transfer the plasma portion to the point-of-care testing device 24 without further manipulation. This enables collection and transfer of plasma to the point-of-care testing device 24 without exposure to blood. Further, for tests which only require small amounts of blood, it eliminates the waste associated with blood collection and plasma separation with an evacuated tube. Also, the blood sampling transfer device 10 of the present disclosure incorporates the concepts of lancing, blood collection, and blood separation.

Figure 3:
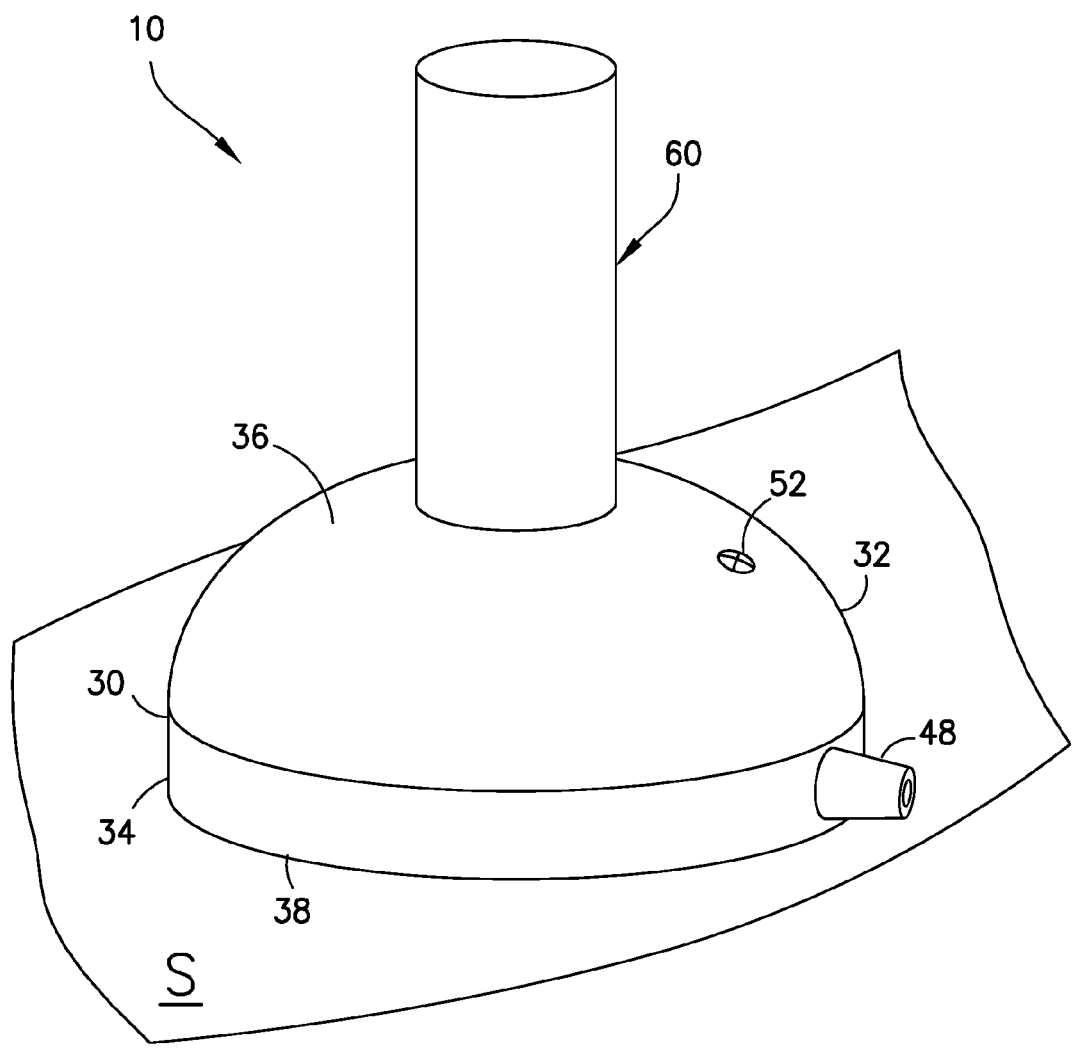
FIG. 3 is a perspective view of a biological fluid sampling transfer device secured to a patient with a housing in an undeformed position in accordance with an embodiment of the present invention.
Figure 4:
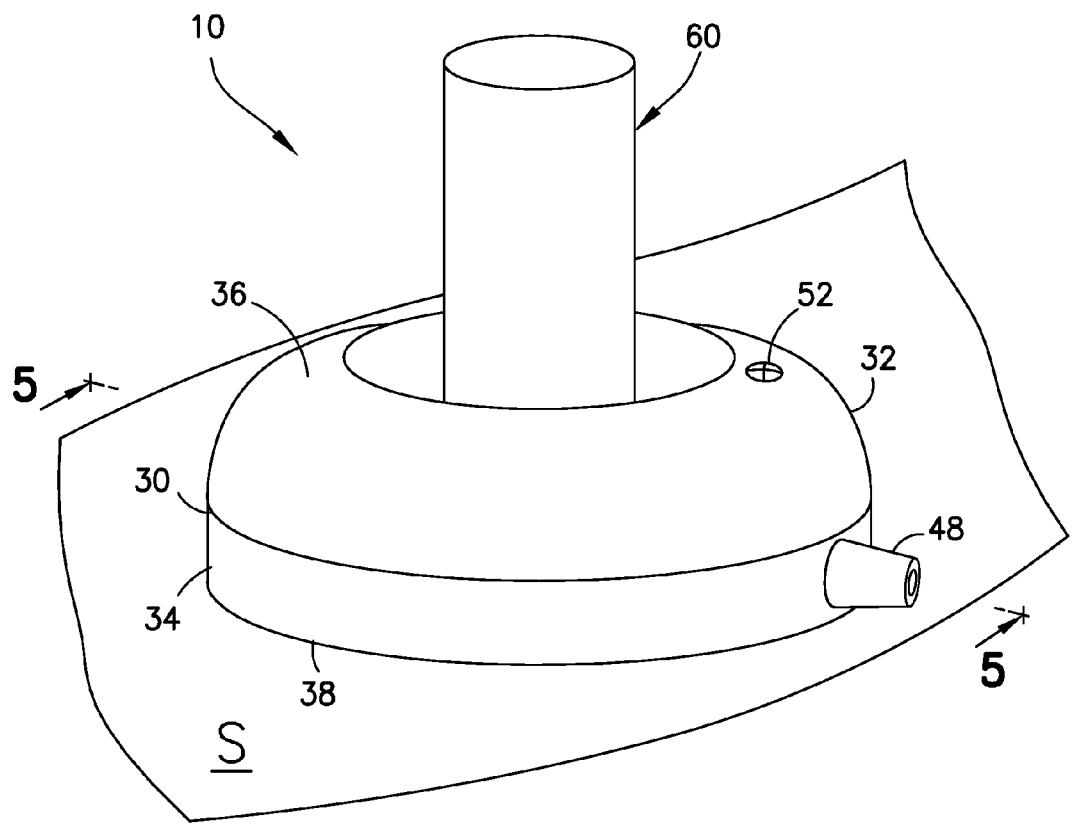
FIG. 4 is a perspective view of a biological fluid sampling transfer device secured to a patient with a housing in a deformed position in accordance with an embodiment of the present invention.
Figure 5:
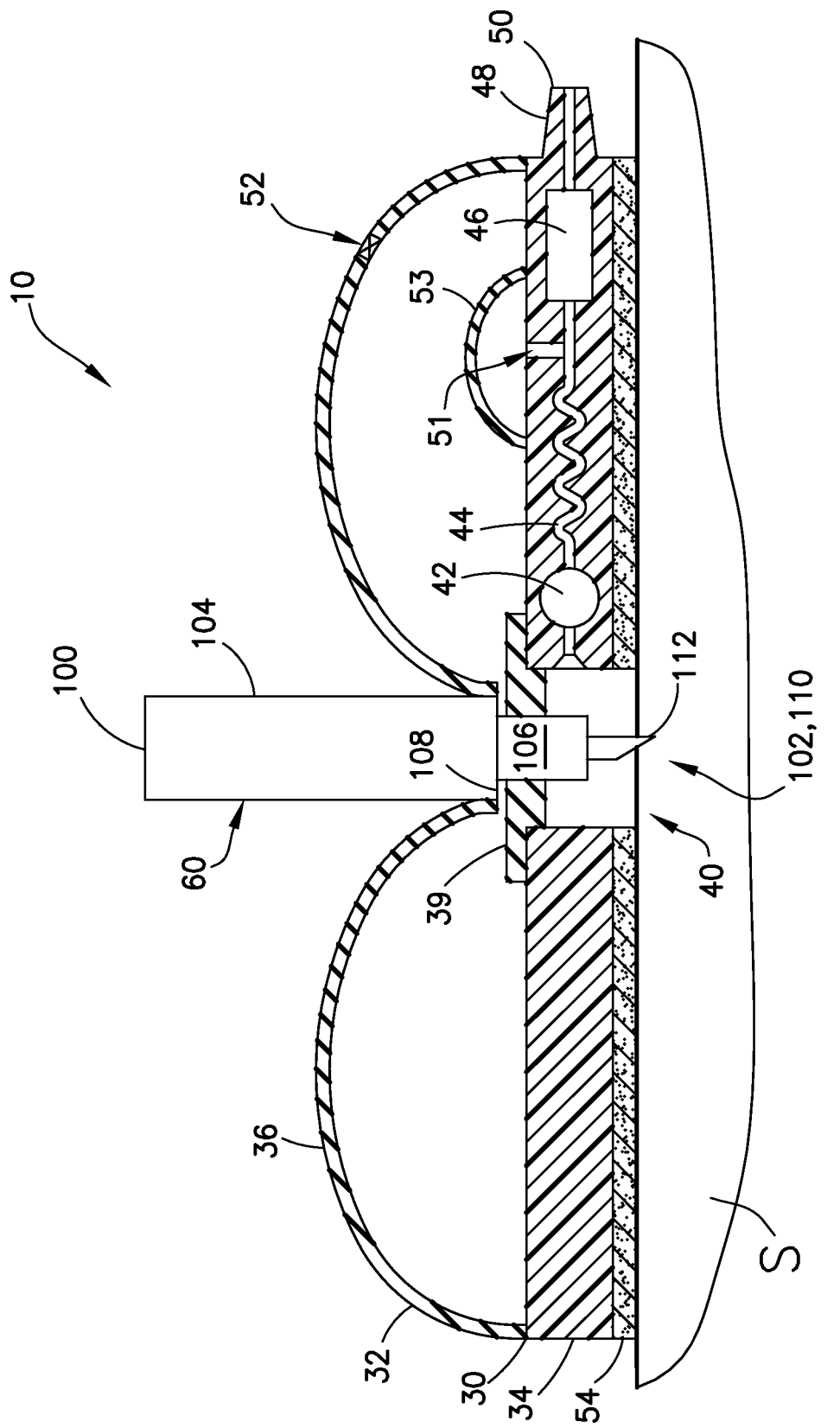
FIG. 5 is a cross-sectional view of the biological fluid sampling transfer device of FIG. 4 in accordance with an embodiment of the present invention.
Figure 6:
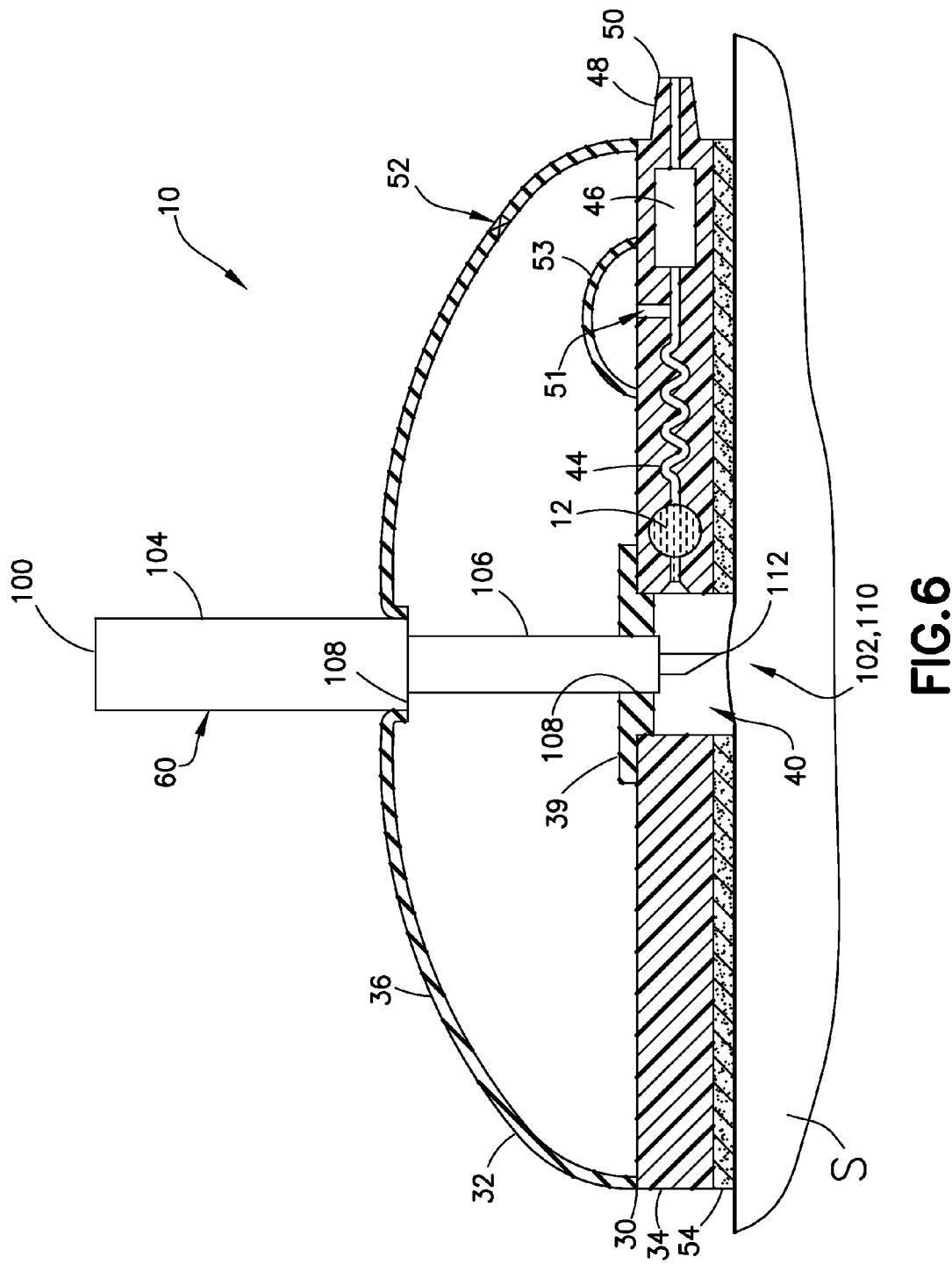
FIG. 6 is a cross-sectional view of the biological fluid sampling transfer device of FIG. 3 with a blood sample received within the biological fluid sampling transfer device in accordance with an embodiment of the present invention.

Referring to FIGS. 1-7, the blood sampling transfer device 10 generally includes a housing 30 having an upper portion 32 and a lower portion 34 removably connectable to the upper portion 32. With the lower portion 34 connected to the upper portion 32, significant relative movement between the upper portion 32 and the lower portion 34 is prevented. The housing 30 defines a central aperture 35 therethrough the upper portion 32 and the lower portion 34. A lancet structure or lancet device 60 is positioned within the central aperture 35 as shown in FIGS. 1-6. The housing 30 includes a lancet engagement portion 39 for securing the lancet structure 60 within the central aperture 35 as shown in FIGS. 5 and 6.

The upper portion 32 includes a dome-shaped surface 36 and the lower portion 34 includes a bottom surface 38. Referring to FIGS. 3, 5, and 6, the bottom surface 38 includes an adhesive 54 so that the blood sampling transfer device 10 can be secured onto a skin surface S of a patient where a blood sample will be accessed. In one embodiment, the adhesive 54 of the bottom surface 38 is protected by a peel-off layer, similar to an adhesive bandage, which would be removed before placing the blood sampling transfer device 10 on the skin surface S of the patient's body. A hydrogel or other layer could be included to provide some thickness to the bottom surface 38 of the lower portion 34 and help improve the stability of the adhesive seal. Additionally, in one embodiment, the adhesive 54 could include a chemistry to create a more liquid-tight seal, similar to painter's tape technology, where wetting from the paint itself causes a chemical reaction with the adhesive 54 to create a more water-tight barrier to prevent the paint from seeping under the tape.

The upper portion 32 is a resiliently deformable member that is transitionable between an undeformed position (FIGS. 3 and 6) and a deformed position (FIGS. 4 and 5) as will be discussed in more detail below. The upper portion 32 is formed of a flexible material such that the upper portion 32 can be depressed by pressure applied by a user. After the pressure is removed, the upper portion 32 returns to its original or undeformed position and its domed-shape. In one embodiment, the upper portion 32 of the housing 30 includes a vent or check valve 52 to allow air to be expelled upon depression of the dome-shaped upper portion 32.

Referring to FIGS. 1-7, the lower portion 34 of the housing 30 of the blood sampling transfer device 10 generally includes an inlet port 40 defined through the bottom surface 38 of the lower portion 34, an entry reservoir 42 in fluid communication with the inlet port 40, a flow channel or mixing channel 44 in fluid communication with the entry reservoir 42, an exit reservoir 46 in fluid communication with the flow channel 44, an exit port or outlet port 48 in fluid communication with the exit reservoir 46, a valve 50 (FIGS. 11 and 12) disposed in communication with the exit port 48, a venting portion 51, and a button portion 53. In one embodiment, the plasma portion 16 contained within the exit reservoir 46 of the lower portion 34 can be transferred through the valve 50 to the point-of-care testing device 24 by pressing the button portion 53 of the lower portion 34 as discussed below.

The lower portion 34 of the housing 30 of the blood sampling transfer device 10 is adapted to contain a sample stabilizer to provide passive and fast mixing of a blood sample with the sample stabilizer. The sample stabilizer, can be an anticoagulant, or a substance designed to preserve a specific element within the blood such as, for example, RNA, protein analyte, or other element. In one embodiment, the sample stabilizer is provided within the flow channel 44. In other embodiments, the sample stabilizer is provided in other areas of the lower portion 34 of the housing 30 of the blood sampling transfer device 10 such as the entry reservoir 42.

In one embodiment, the flow channel 44 comprises a serpentine shape to promote efficient mixing of a blood sample 12 (FIGS. 6, 7, and 9) having a cellular portion 14 and a plasma portion 16. As discussed below, a blood separation device 22 provides a rotational force applied to the lower portion 34 of the housing 30 to separate the plasma portion 16 from the cellular portion 14 through the flow channel 44. In other embodiments, the flow channel 44 comprises other shapes to promote efficient mixing of a blood sample.

The valve 50 is transitionable between a closed position (FIG. 11) to seal a plasma portion 16 of the blood sample 12 within the exit reservoir 46 of the lower portion 34 of the housing 30 and an open position (FIG. 12) to allow a plasma portion 16 to flow through the exit port 48 to a point-of-care testing device 24 as shown in FIG. 10.

Referring to FIGS. 11 and 12, the exit port or outlet port 48 of the lower portion 34 of the housing 30 of the blood sampling transfer device 10 may include a valve 50 that is transitionable between a closed position and an open position. With the valve 50 in an open position, the plasma portion 16 of the blood sample 12 may flow through the outlet port 48 to a blood testing device or a point-of-care testing device 24 (FIG. 10).

In one embodiment, referring to FIGS. 11 and 12, the valve 50 may generally include a transfer channel 90, a bellows or deformable wall member 92, and a septum or barrier 94 having a first barrier wall 96 and a second barrier wall 98. Referring to FIG. 11, the valve 50 is in a closed position to prevent the plasma portion 16 of the blood sample 12 from flowing through the outlet port 48. In this manner, the plasma portion 16 is sealed within the lower portion 34 of the housing 30 of the blood sampling transfer device 10. Referring to FIG. 12, the valve 50 is in an open position so that the plasma portion 16 of the blood sample 12 may flow through the outlet port 48 to a blood testing device or a point-of-care testing device 24 (FIG. 10).

Referring to FIG. 11, with the plasma portion 16 received within the exit reservoir 46 of the lower portion 34 of the blood sampling transfer device 10, the outlet port 48 of the lower portion 34 of the blood sampling transfer device 10 is then positioned over a receiving port 26 of the point-of-care testing device 24. Pushing down in the direction of arrow B compresses the deformable wall member 92 and opens up the first barrier wall 96 and the second barrier wall 98 of the septum 94 as shown in FIG. 12. With the valve 50 in the open position, the plasma portion 16 of the blood sample 12 is allowed to flow through the receiving port 26 to the point-of-care testing device 24 in a closed manner reducing exposure to the clinician and the patient.

The valve 50 of the blood sampling transfer device 10 only opens when the outlet port 48 is pressed upon the receiving port 26 of the point-of-care testing device 24. This releases the isolated plasma portion 16 directly into the receiving port 26 of the point-of-care testing device 24, thus mitigating unnecessary exposure to the patient's blood.

Referring to FIGS. 1-6, the blood sampling transfer device 10 also includes a lancet or lancet structure 60 that may be secured within the central aperture 35 of the housing 30. The lancet 60 generally includes a first end 100, a second end 102, a top or handle portion 104 adjacent the first end 100, a bottom or lancet portion 106 adjacent the second end 102, and a housing engagement portion 108. The housing engagement portion 108 engages the lancet engagement portion 39 of the housing for securing the lancet 60 to the housing 30 within central aperture 35 as shown in FIGS. 5 and 6. Referring to FIGS. 5 and 6, a portion of the lancet 60 is disposed within the housing 30 of the blood sampling transfer device 10. The lancet portion 106 includes a puncturing element 110 having a puncturing end 112. The puncturing end 112 is adapted for puncturing the skin surface S of a patient (FIG. 5), and may define a pointed end, a blade edge, or a similar cutting mechanism. The puncturing end 112 may include a preferred alignment orientation, such as with a pointed end of a blade aligned in a specific orientation.

The lancet 60 is adapted for movement between a pre-actuated position (FIGS. 3 and 6) wherein the puncturing element 110 including the puncturing end 112 is retained within the housing 30 and a puncturing position (FIGS. 4 and 5) wherein the puncturing end 112 of the puncturing element 110 extends through the inlet port 40 of the housing 30 to puncture a skin surface S of a patient to draw a blood sample as discussed in more detail below.

In one embodiment, the housing 30 of the blood sampling device 10 may include a self-sealing dock that would allow an external lancet to be removably received within the housing 30. The external lancet could be either pre-integrated into the packaged device or introduced separately by a user before using the blood sampling transfer device 10 of the present disclosure.

Referring to FIG. 8, a blood separation device or centrifuge 22 of the present disclosure generally includes a receiving port 120 adapted to receive the lower portion 34 of the blood sampling transfer device 10 such that with the lower portion 34 received within the centrifuge 22 and a rotational force applied to the lower portion 34, a plasma portion 16 of the blood sample 12 is separated from a cellular portion 14 of the blood sample 12 (FIG. 9). The centrifuge 22 includes a receiving port 120 adapted to receive the lower portion 34 of the blood sampling transfer device 10, a base or bottom portion 122, a top portion 124 movably connected to the base portion 122 by a hinged portion 126, and a rotational force element 128 contained within the base portion 122. The top portion 124 is transitionable between an open position in which the lower portion 34 of the blood sampling transfer device 10 can be placed within the receiving port 120 as shown in FIG. 8 and a closed position. With the lower portion 34 of the blood sampling transfer device 10 received within the centrifuge 22, a rotational force is applied to the lower portion 34 of the blood sampling transfer device 10 to separate the plasma portion 16 from the cellular portion 14 as described in more detail below.

Referring to FIG. 10, a blood testing device or point-of-care testing device 24 includes a receiving port 26 for receiving the outlet port 48 of the lower portion 34 of the housing 30 of the blood sampling transfer device 10. The blood testing device 24 is adapted to receive the lower portion 34 of the housing 30 to analyze the blood sample and obtain test results. The receiving port 26 of the point-of-care testing device 24 allows for the closed transfer of a blood sample from the lower portion 34 of the housing 30 to the point-of-care testing device 24.

Referring to FIGS. 1-10, use of a blood sampling transfer device of the present disclosure will now be described. Referring to FIGS. 3 and 6, upon selecting a site, a clinician can adhere the adhesive 54 on the bottom surface 38 of the lower portion 34 of the housing 30 onto a skin surface S of a patient where a blood sample will be accessed over a selected sampling site.

Referring to FIGS. 3-6, a user or an operator may then apply pressure to the dome-shaped surface 36 of the upper portion 32 of the housing 30 to actuate the upper portion 32 from the undeformed position (FIGS. 3 and 6) to the deformed position (FIGS. 4 and 5). Actuation of the upper portion 32 from the undeformed position (FIGS. 3 and 6) to the deformed position (FIGS. 4 and 5) moves the lancet 60 from the pre-actuation position (FIGS. 3 and 6) to the puncturing position (FIGS. 4 and 5) thereby causing the lancing of the skin surface S of the patient by the puncturing end 112 of the lancet 60 as shown in FIG. 5. When the upper portion 32 of the housing 30 is depressed, the puncturing end 112 of the lancet 60 cuts into the skin surface S of the patient's body and capillary blood begins to flow into the inlet port 40 of the housing 30.

After lancing and release of the pressure for the lancing action, the domed shape of the upper portion 32 begins to relax and returns to its original shape or undeformed position. This return of the upper portion 32 to its undeformed position creates a gentle vacuum during the process that helps to draw out the capillary blood through the inlet port 40 and to the entry reservoir 42 of the lower portion 34 of the housing 30.

Figure 7:
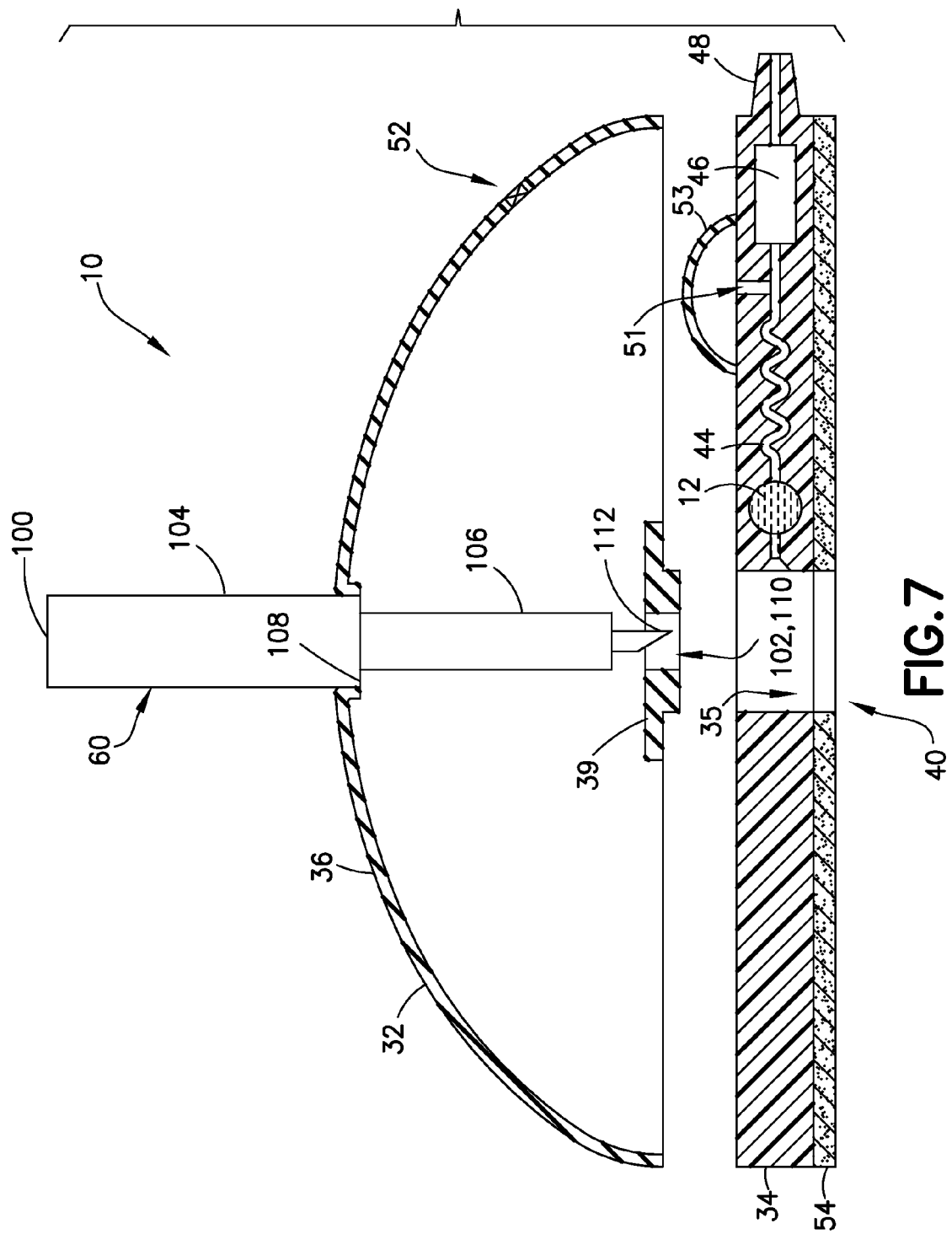
FIG. 7 is a cross-sectional view of the biological fluid sampling transfer device of FIG. 6 in accordance with an embodiment of the present invention, with an upper portion of the housing removed from a lower portion of the biological fluid sampling transfer device.

With the upper portion 32 of the housing 30 returned to its undeformed position and with the blood sample 12 received within the entry reservoir 42 as shown in FIG. 6, the clinician can remove the lower portion 34 of the housing 30 from the upper portion 32 as shown in FIG. 7. When the lower portion 34 is removed from the upper portion 32, the entry reservoir 42 and the flow channel 44 of the lower portion 34 is sealed from the external environment. Additionally, with the lower portion 34 removed from the upper portion 32, the puncturing end 112 of the lancet 60 is contained within the upper portion 32 to shield the puncturing end 112.

Referring to FIG. 8, the next step of the process involves manual insertion of the lower portion 34 into a blood separation device or centrifuge 22 designed specifically for the lower portion 34 of the housing 30. The centrifuge 22 is designed to facilitate plasma separation by centrifugal force and to drive a blood sample through the mixing channel 44 of the lower portion 34. The blood sample 12 contained within the lower portion 34 is quickly spun in the centrifuge 22 and due to the low volume is separated through the mixing channel 44 of the lower portion 34 within a few seconds such that the plasma portion 16 is collected within the exit reservoir 46 of the lower portion 34. After separation, the lower portion 34 is removed manually from the centrifuge device 22.

Thereafter, referring to FIG. 10, the collected plasma portion 16 of the blood sample 12 within the exit reservoir 46 of the lower portion 34 of the blood sampling transfer device 10 is transferred to the receiving port 26 of the point-of-care testing device 24 to analyze the collected plasma portion 16 and obtain test results for tests such as glucose, cholesterol, or other blood sample results. Referring to FIG. 10, the receiving port 26 of the point-of-care testing device 24 allows for the closed transfer of a portion of the plasma portion 16 of the blood sample 12 from the lower portion 34 to the point-of-care testing device 24.

In one embodiment, the plasma portion 16 of the blood sample 12 within the exit reservoir 46 of the lower portion 34 is dispensed through the valve 50 of the exit port 48 of the lower portion 34 into a well or receiving port 26 of the point-of-care testing device 24 to perform the desired test. In one embodiment, the plasma portion 16 is transferred through the valve 50 to the point-of-care testing device 24 by pressing the button portion 53 of the lower portion 34. In another embodiment, the lower portion 34 can be connected to the upper portion 32 and actuation of the upper portion 32 from the undeformed position to the deformed position transfers the plasma portion 16 of the blood sample 12 from the lower portion 34 of the blood sampling transfer device 10 to the blood testing device 24 via the outlet port 48.

In one embodiment, the entry reservoir 42 and/or flow channel 44 of the lower portion 34 of the housing 30 contains the sample stabilizer to promote efficient mixing with the blood sample. Referring to FIG. 5, upon actuation of the lancet 60 to puncture the skin surface S, no or minimal blood will seep between the stick site and the housing 30 of the blood sampling transfer device 10, and, importantly, any seeped blood will not subsequently enter the blood sampling transfer device 10.

Some of the advantages of the blood sampling transfer device and the blood separation and testing system of the present disclosure over prior systems are that it is a closed system which reduces blood sample exposure, it provides passive and fast mixing of the blood sample with a sample stabilizer, and it is capable of transferring pure plasma to the point-of-care testing device 24. The clinician may collect and separate the blood sample and then immediately transfer the plasma portion to the point-of-care testing device 24 without further manipulation. This enables collection and transfer of plasma to the point-of-care testing device 24 without exposure to blood. Further, for tests which only require small amounts of blood, it eliminates the waste associated with blood collection and plasma separation with an evacuated tube. Also, the blood sampling transfer device 10 of the present disclosure incorporates the concepts of lancing, blood collection, and blood separation.

While this disclosure has been described as having exemplary designs, the present disclosure can be further modified within the spirit and scope of this disclosure. This application is therefore intended to cover any variations, uses, or adaptations of the disclosure using its general principles. Further, this application is intended to cover such departures from the present disclosure as come within known or customary practice in the art to which this disclosure pertains and which fall within the limits of the appended claims.

What is claimed is:

1. A biological fluid sampling transfer device, comprising:
   a housing having a resiliently deformable upper portion, a lower portion removably connectable to the upper portion, the lower portion having an inlet port, an outlet port, and a flow channel, the inlet port and the outlet port in fluid communication via the flow channel, the upper portion transitionable between an undeformed position and a deformed position; and
   a puncturing element, a portion of which is disposed within the housing and adapted for movement between a pre-actuated position wherein the puncturing element is retained within the housing and a puncturing position wherein the puncturing element extends through the inlet port of the lower portion of the housing,
   wherein, when the lower portion of the housing is removed from the upper portion of the housing, the inlet port and the flow channel in the lower portion are sealed and the puncturing element is contained within the upper portion of the housing.

2. The biological fluid sampling transfer device of claim 1, wherein the biological fluid sampling transfer device is adapted to receive a multi-component blood sample.

3. The biological fluid sampling transfer device of claim 2, wherein the multi-component blood sample comprises a first cellular component and a second plasma component.

4. The biological fluid sampling transfer device of claim 2, wherein the flow channel is adapted to receive the blood sample via the inlet port.

5. The biological fluid sampling transfer device of claim 1, wherein actuation of the upper portion from the undeformed position to the deformed position moves the puncturing element from a pre-actuated position to a puncturing position.

6. The biological fluid sampling transfer device of claim 5, wherein after the puncturing element moves to the puncturing position, the upper portion returns to its undeformed position and returns the puncturing element to the pre-actuated position.

7. The biological fluid sampling transfer device of claim 6, wherein with the blood sample received within the flow channel, the lower portion is removable from the upper portion.

8. The biological fluid sampling transfer device of claim 1, further comprising an adhesive disposed on an outside surface of the lower portion.

9. The biological fluid sampling transfer device of claim 1, further comprising a check valve in the upper portion.

10. A biological fluid sampling transfer device adapted to receive a multi-component blood sample, the biological fluid sampling transfer device comprising:
    a housing having a resiliently deformable upper portion, a lower portion removably connectable to the upper portion, the lower portion having an inlet port, an outlet port, and a flow channel, the inlet port and the outlet port in fluid communication via the flow channel, the flow channel adapted to receive the blood sample via the inlet port, the upper portion transitionable between an undeformed position and a deformed position; and
    a puncturing element, a portion of which is disposed within the housing and adapted for movement between a pre-actuated position wherein the puncturing element is retained within the housing and a puncturing position wherein the puncturing element extends through the inlet port of the lower portion of the housing,
    wherein actuation of the upper portion from the undeformed position to the deformed position moves the puncturing element from the pre-actuated position to the puncturing position,
    wherein after the puncturing element moves to the puncturing position, the upper portion returns to the undeformed position and the puncturing element returns to the pre-actuated position, and
    wherein, when the lower portion of the housing is removed from the upper portion of the housing, the inlet port and the flow channel in the lower portion are sealed and the puncturing element is contained within the upper portion of the housing.

11. The biological fluid sampling transfer device of claim 10, wherein with the blood sample received within the flow channel, the lower portion is removable from the upper portion.

12. The biological fluid sampling transfer device of claim 10, further comprising an adhesive disposed on an outside surface of the lower portion.

13. The biological fluid sampling transfer device of claim 10, further comprising a check valve in the upper portion.

* * * * *